(12) United States Patent
Soltis et al.

(10) Patent No.: US 6,360,583 B1
(45) Date of Patent: Mar. 26, 2002

(54) OXYGEN SENSOR MONITORING

(75) Inventors: Richard E. Soltis, Saline; Tie Wang, Troy, both of MI (US)

(73) Assignee: Ford Global Technologies, Inc., Dearborn, MI (US)

( * ) Notice: Subject to any disclaimer, the term of this patent is extended or adjusted under 35 U.S.C. 154(b) by 0 days.

(21) Appl. No.: 09/200,946

(22) Filed: Nov. 30, 1998

(51) Int. Cl.[7] .................. G01N 7/00; G01N 33/497
(52) U.S. Cl. ....................................... 73/23.31
(58) Field of Search .................. 73/23.31, 35, 23.32, 73/117.3, 118.1, 116, 861.17; 60/276, 274; 123/425

(56) References Cited

U.S. PATENT DOCUMENTS

| 4,846,130 A | * | 7/1989 | Jenson ..................... 73/35 |
| 5,052,361 A | | 10/1991 | Ono et al. ................ 73/118.2 |
| 5,154,054 A | | 10/1992 | Nakane et al. ............ 60/276 |
| 5,179,929 A | | 1/1993 | Miyashita et al. ......... 123/688 |
| 5,206,809 A | * | 4/1993 | Iwakiri et al. ............ 73/117.3 |
| 5,243,954 A | | 9/1993 | Moss ..................... 123/688 |
| 5,251,604 A | | 10/1993 | Kaneko et al. ............ 123/688 |
| 5,391,282 A | | 2/1995 | Miyashita et al. .......... 204/401 |
| 5,396,765 A | * | 3/1995 | Maruyama et al. .......... 60/276 |
| 5,485,382 A | * | 1/1996 | Seki et al. ............. 364/431.05 |
| 5,558,752 A | | 9/1996 | Wang et al. |
| 5,996,337 A | * | 12/1999 | Blosser et al. ............. 60/274 |
| 6,026,639 A | * | 2/2000 | Seki et al. ................ 60/274 |

FOREIGN PATENT DOCUMENTS

DE    43 42 136 A    6/1995

* cited by examiner

Primary Examiner—Benjamin R. Fuller
Assistant Examiner—Octavia Davis
(74) Attorney, Agent, or Firm—Jerome R. Drouillard

(57) ABSTRACT

A gas sensor deterioration monitor, particularly suited for use in an exhaust stream from an internal combustion engine. Under certain engine operating conditions, the output signal from the sensor is transformed through a Fourier Transformation into a frequency domain signal. Ratios of the magnitudes of certain odd and even harmonics are compared to corresponding reference values for a new sensor. Deviations beyond certain limits indicate a sensor that has deteriorated substantially.

20 Claims, 5 Drawing Sheets

OXYGEN SENSOR MONITORING

FIELD OF THE INVENTION

The present invention relates to gas sensors mounted in the exhaust stream of an engine and more particularly to monitoring the deterioration of the sensors.

BACKGROUND OF THE INVENTION

Oxygen sensors are employed in various applications to determine the oxygen content for a stream of gas as it flows past the sensor. One example of such an application is the use of an oxygen sensor mounted in the exhaust stream from an internal combustion engine. By monitoring the exhaust stream, one can determine various characteristics of the combustion events within the engine.

The information gained from the oxygen sensor can then be used, for example, as feedback control of the air/fuel (A/F) ratio. The A/F control allows for engine operation to be maintained around stoichiometry where emissions are most effectively reduced with a typical catalytic converter.

One example of such an oxygen sensor is a zirconium-oxide (ZrO2) oxygen sensor. This sensor is made up of a yttrium doped ZrO2 ceramic, with two sides of the ceramic covered with a respective one of two electrodes, usually platinum, to form an electrochemical cell. A porous layer may also be located on one or both of the electrodes. The performance of an oxygen sensor comprises both static and transient characteristics. The static characteristics of a zirconia oxygen sensor are defined by the magnitudes of the voltages for rich and lean readings and the switching point of the sensor. The transient characteristics of a zirconia oxygen sensor are defined by the response times.

The response times of the sensor define the transient characteristics of an oxygen sensor. The response times are a measurement of the times that an oxygen sensor needs to switch from high voltage (rich state of the exhaust) to a low voltage (lean state of the exhaust), or vice versa. The effects of varying response times are manifested in the limit-cycle frequency of the A/F modulation. An oxygen sensor with shorter response times generally results in an A/F ratio that remains closer to the desired value.

As a sensor ages, however, build up of contaminates may occur on the sensor, thus causing a deterioration in the response time, and thus the effectiveness of the sensor. How much deterioration must occur before a sensor becomes unacceptable is difficult to quantify. Thus, it is desirable to have a way to detect and quantify the deterioration of an oxygen sensor as it ages, in order to determine when it becomes unacceptable for its intended purpose.

SUMMARY OF THE INVENTION

In its embodiments, the present invention contemplates a method of monitoring the deterioration of a sensor in an exhaust stream of an engine. The method includes the steps of: operating the engine under a condition where the oscillation frequency of air/fuel ratio between rich and lean is determined; receiving a signal from the sensor; performing a Fourier Transform on the signal to produce a frequency domain signal having even and odd order harmonics; calculating the magnitude of one of the odd order harmonics and one of the even order harmonics; calculating a ratio of the odd order harmonic to the even order harmonic; and comparing the ratio to an acceptable range of values.

Accordingly, an object of the present invention is to monitor the deterioration of an oxygen sensor as it ages by employing a Power Density Analysis of a Fourier Transform to the output signal from the sensor.

An advantage of the present invention is that the deterioration of one or more oxygen sensors can be monitored by a relatively simple process with a high degree of accuracy.

Another advantage of the present invention is that it can be employed while the engine operates under a fixed (forced) air/fuel modulation frequency, or, if desired, under a closed-loop limit-cycle control with proper baseline calculation.

A further advantage of the present invention is that multiple sets of different order harmonic ratios can be employed to assure that a false failure output is not generated.

DETAILED DESCRIPTION OF THE PREFERRED EMBODIMENTS

Figure 1:
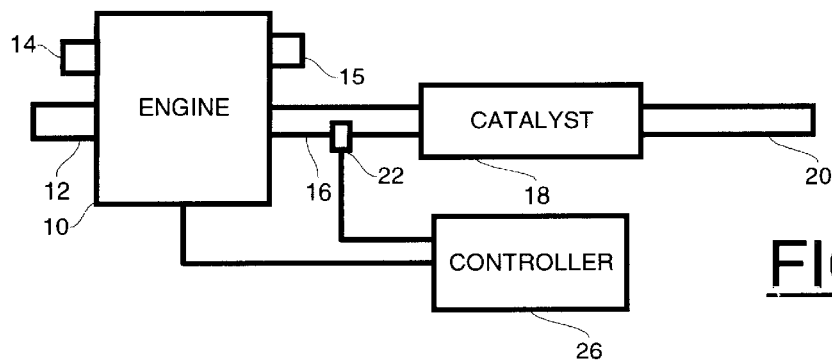
FIG. 1 is a schematic diagram showing an oxygen sensor mounted in the exhaust stream of a vehicle.

FIG. 1 shows an engine 10 having an air intake 12, a fuel system 14, a spark (ignition) assembly 15, and an exhaust conduit 16 for receiving the exhaust from combustion events. The exhaust conduit 16 connects to a catalytic converter 18, through which the exhaust flows, which in turn connects to another exhaust conduit 20 downstream of the catalyst 18. Mounted in the first exhaust conduit 16 is an oxygen sensor 22. The oxygen sensor can be any one of several different kinds of sensors which respond to exhaust gas oxygen, and include universal exhaust gas oxygen (UEGO) sensors, used in the exhaust systems of vehicles and known to those skilled in the art, and is preferably a zirconia based oxygen sensor, although it need not be. The oxygen sensor 22 is in communication with an engine controller 26, which is also in communication with mechanisms on the engine 10 for controlling the intake of fuel and/or air, and spark timing, among other functions.

Figure 2A:
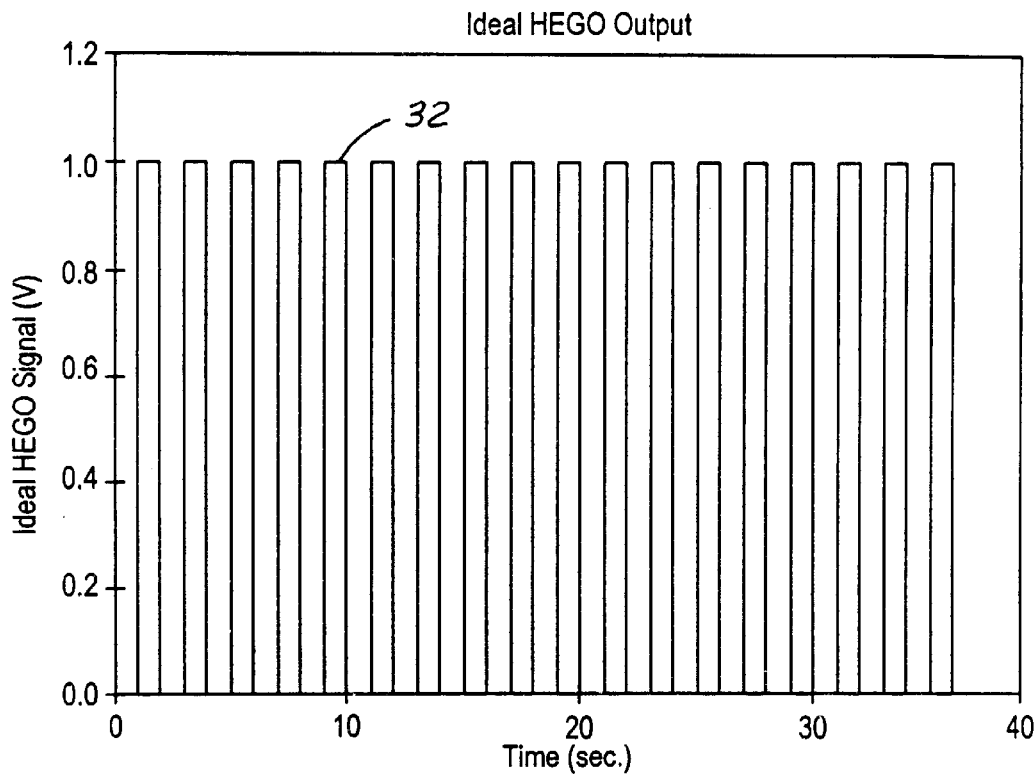
FIG. 2A is an example of an ideal square wave for an exhaust gas oxygen sensor in the time domain.
Figure 2B:
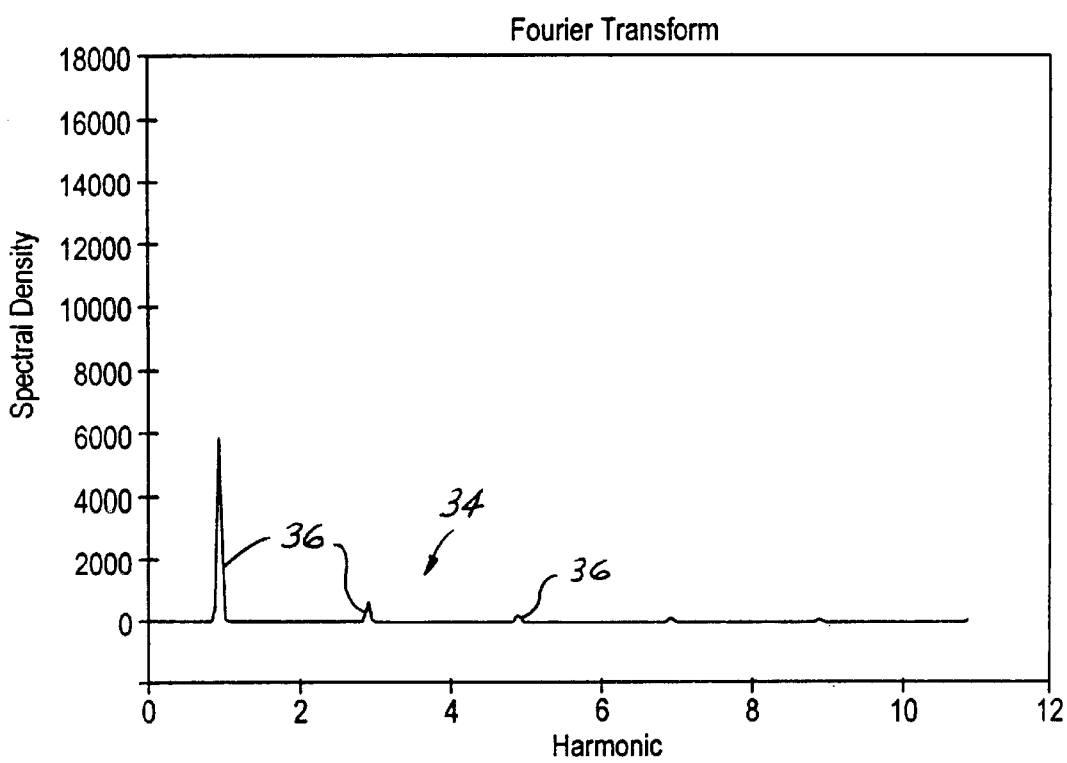
FIG. 2B is an example of a frequency domain signal after employing a Fast Fourier Transform on the ideal square wave of FIG. 2A.

FIG. 2A shows an example of an ideal square wave signal 32 in the time domain, while FIG. 2B shows the corresponding frequency domain signal 34 after undergoing a FFT. One will note that, for an ideal square wave, there are only odd order frequency terms 36 that result from the FFT. Thus, for an ideal sensor that produces a signal which switches exactly as a square wave there are also only odd order harmonic terms. On the other hand, for those with signals that deviate from an ideal square wave, even order harmonic terms will also appear. This information, then, can be used to detect deterioration in a sensor that, if perfect, would produce a signal in the form of an ideal square wave. Of course, real sensors will have some real world time lags for switching and other factors that will result in a signal that is other than ideal. However, by determining how far from ideal the frequency signal is for a new sensor, one can compare this to an aged sensor to determine the extent of deterioration that has occurred.

Figure 3:
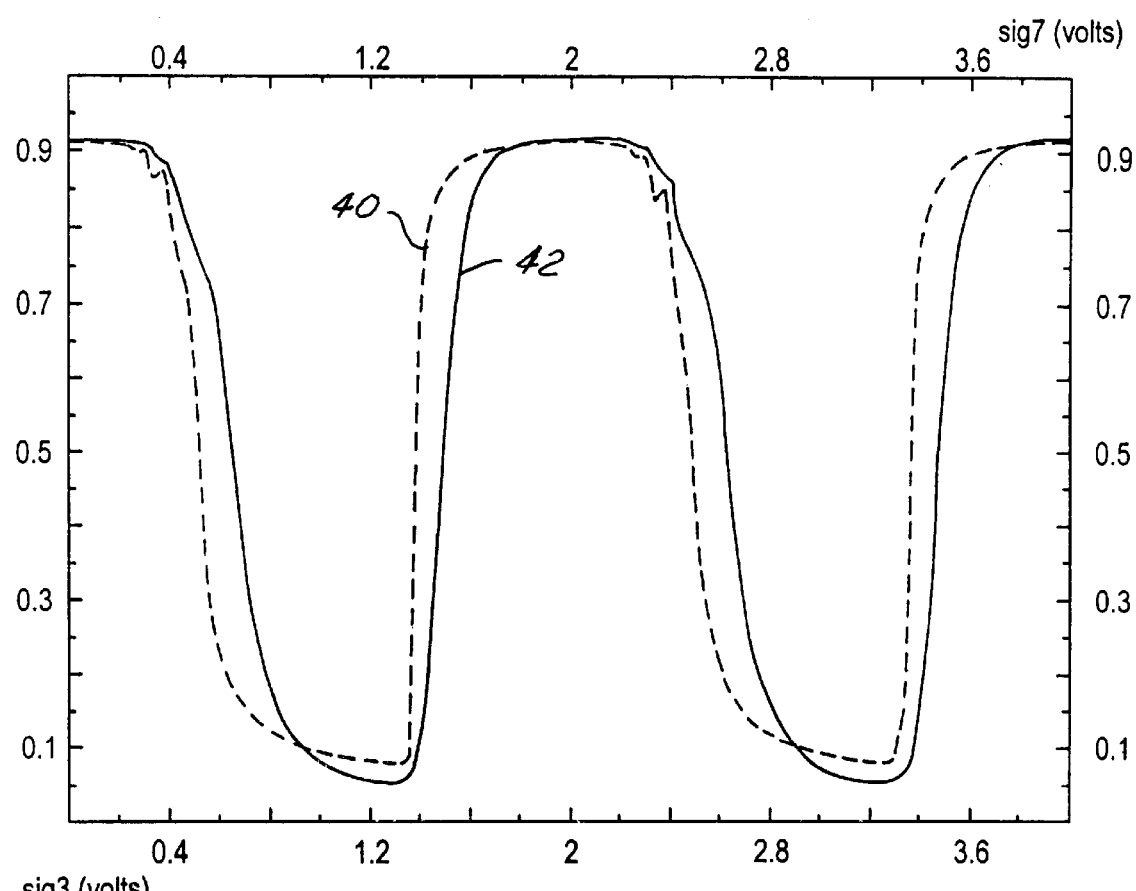
FIG. 3 is a graphical representation of the voltage versus time for a sampled new and an aged oxygen sensor.

FIG. 3 illustrates an example of a comparison of the time domain signals for a sample of signal output for a new and an aged sensor; it is a graphical representation, of voltage output versus time, comparing signal 40 from a new oxygen sensor and a signal 42 from an oxygen sensor that has operated through about 11,000 miles of engine operation in a vehicle. One will note that while the signal 42 from the aged sensor lags and varies in other ways the signal 40 from the new sensor, that quantifying this change is a difficult proposition. With a signal after a FFT, discrete magnitudes for the various harmonics are available. These discrete values, then, can be employed to determine the deterioration of a sensor over time.

Figure 4:
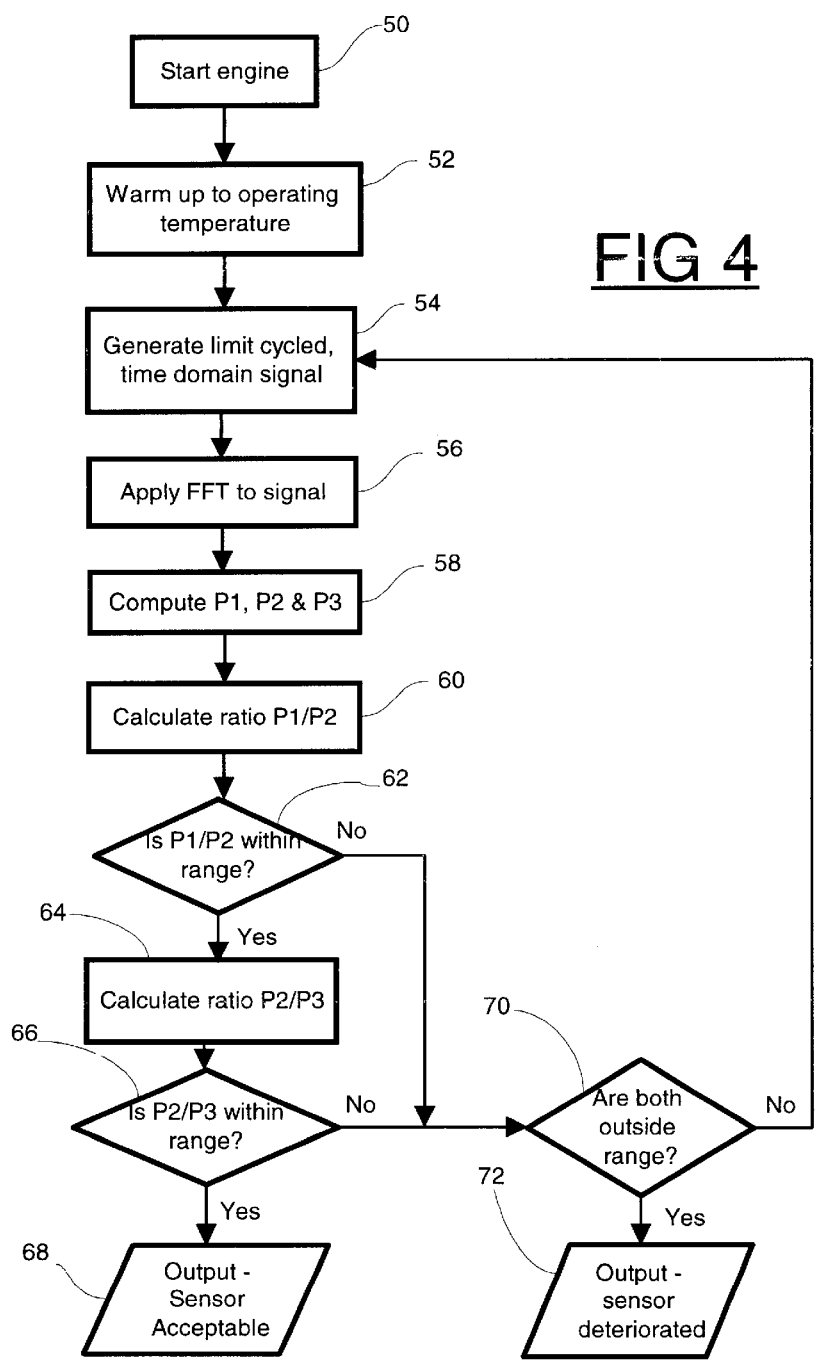
FIG. 4 is a flow chart for the method of monitoring the deterioration of the oxygen sensor, according to the present invention.

FIG. 4 illustrates a flow chart of the process for monitoring an oxygen sensor to determine when sufficient deterioration of the sensor has occurred to indicate sensor failure. The test is carried out during engine operation, step 50, preferably after the engine has warmed up to within the normal operating range, step 52. The intervals at which the deterioration test are carried out depend upon the requirements for a particular engine and vehicle.

To begin the testing, the engine is operated so that a limit cycled, time domain signal is produced by the sensor, step 54. This signal may be produced in two ways. First, the engine controller may force the engine operation to switch between rich and lean air/fuel ratios at a predetermined frequency, a forced oscillation mode. In this way, knowing where the peaks should occur in the FFT signal will be easy. Or second, the signal may also be produced when it is determined that the engine is in steady-state operation, where the frequency of the rich-lean limit cycle can be determined; then the location of the peaks in the FFT signal can be determined.

Next, the time domain oxygen signal, taken over a predetermined time interval, undergoes a FFT to create a frequency domain signal, step 56. From this frequency domain signal, the magnitudes of the first order harmonic, $P_1$, the second order harmonic, $P_2$, and the third order harmonic, $P_3$ are calculated, step 58. A ratio of the first to the second order harmonic, $P_1/P_2$, is then calculated, step 60. This ratio is compared to a predetermined range of acceptable values that have been determined based upon the response that a "new" or "good" sensor would give, step 62. If within the range, then a ratio of the second order harmonic to the third order harmonic, $P_2/P_3$ is calculated, step 64. This ratio is compared to a different predetermined range of acceptable values for a "good" sensor, step 66. If this is also within the range, the sensor is determined to be acceptable, i.e., not excessively deteriorated, step 68. But if either one of the calculated ratios are outside of their respective acceptable ranges, but not both, then the process returns to step 54 to repeat the testing. Step 70. On the other hand, if both are outside of their respective acceptable ranges, then a sensor deterioration output is generated, step 72. This output can take any one of several different forms for notifying the vehicle operator that maintenance work is needed on the vehicle; optionally, one may use this output to adjust the engine control strategy to compensate for the deterioration.

As for using two different ratios to determine sensor failure, the second one is more for backup so that a false sensor failure is not output. This is just one example of how one might accomplish this, and, if desired, one may just rely on a single ratio of odd to even harmonics to determine sensor failure.

Figure 5:
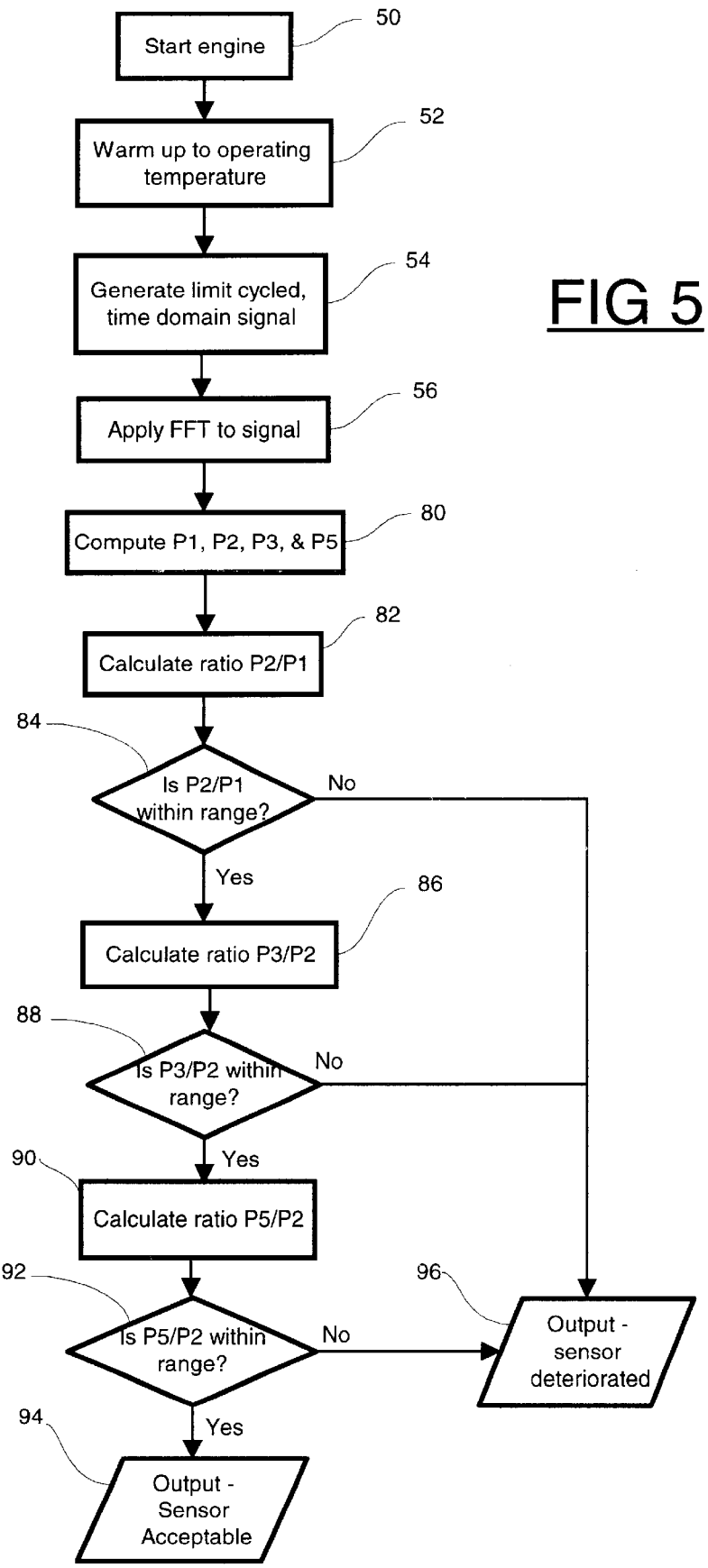
FIG. 5 is a flow chart illustrating an alternate embodiment of the present invention.

FIG. 5 illustrates a flow chart similar to FIG. 3, but illustrating an alternative embodiment of the present invention. For this embodiment, the initial steps (50–56) are the same as with those described in relation to FIG. 4, and will not be discussed again. After the frequency domain signal is generated, the first, $P_1$, second, $P_2$, third, $P_3$, and fifth, $P_5$, harmonics are determined, step 80. The ratio $P_2/P_1$ is calculated, step 82, and this ratio is compared with a predetermined acceptable range, step 84. If it is within the range, then the ratio $P_3/P_2$ is calculated, step 86. It is then compared to a predetermined acceptable range, step 88. If within the range, then the ratio $P_5/P_2$ is calculated, step 90, and compared to its predetermined acceptable range, step 92. If within the acceptable range, then the output reads that the sensor is acceptable, step 94. If, on the other hand, any one of the ratios calculated are outside of its respective range, then a sensor deterioration output is created, step 96.

While the process for the second embodiment outputs failure if any one ratio is outside of its respective range, this is only one example, and the process may be modified so that it requires multiple ratios outside of their respective ranges before a sensor failure is indicated. This depends upon the particular application and desire of one implementing the sensor monitoring process. Generally, if one desires to have a monitoring process with very high sensitivity to deterioration, then ratios that include higher order harmonics may be more desirable. (See the example below in relation to FIGS. 6A and 6B.) However, this will require more accuracy in the measurements initially.

On the other hand, if only gross changes in the sensor response are of interest, then ratios taken for the lower order harmonics will likely be preferred since they are easier to measure due to their large signal values. Again, a combination of ratios can be used in order to check for consistency in order to assure an accurate determination of sensor failure due to deterioration.

Figure 6A:
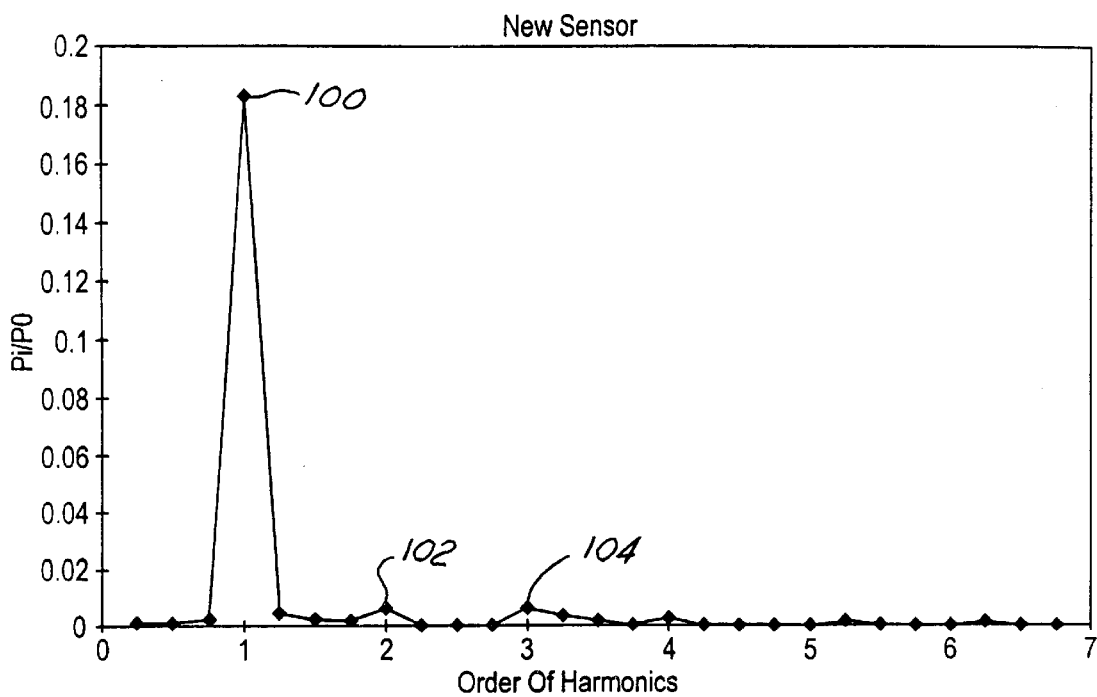
FIG. 6A is a graph illustrating the harmonics of a frequency domain signal after Fast Fourier Transformation of an exemplary time domain signal for a new oxygen sensor.

FIG. 6A is an example illustrating a graphical representation of an oxygen sensor signal in the frequency domain after undergoing a FFT and dividing the magnitudes by the zero order harmonic, for a new oxygen sensor. This includes a very large amplitude for the first order harmonic 100 and a much smaller amplitude at the second order harmonic 102. The third order harmonic 104 has a slightly larger amplitude than at the second order harmonic 102. The higher order harmonics are of much less magnitude. One will note that a new sensor is not necessarily an ideal sensor, since an ideal sensor would have only odd order harmonics. Thus, the comparisons used for deterioration determinations need to account for this.

Figure 6B:
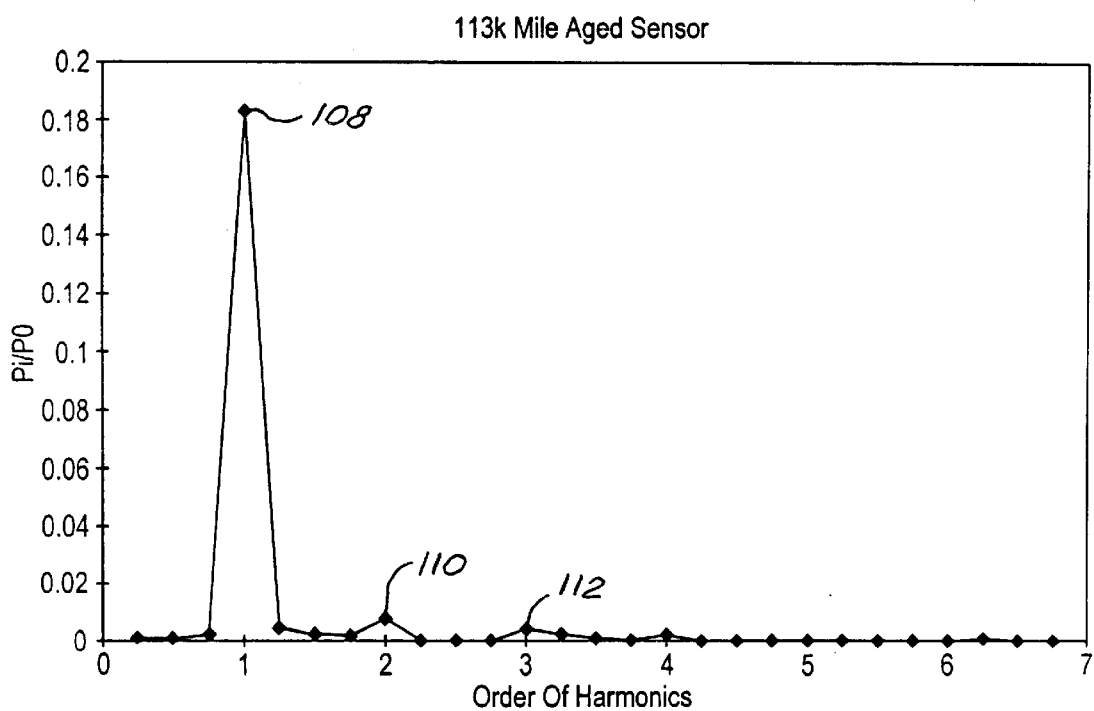
FIG. 6B is a graph illustrating the harmonics of a frequency domain signal after FFT of an exemplary time domain signal for an aged oxygen sensor.

FIG. 6B is a graph similar to FIG. 6A, but for an oxygen sensor that has undergone an aging operation representing engine use for about 113,000 miles of vehicle operation. For this graph, one will note that while the first order harmonic 108 is similar to the first order harmonic 100 in FIG. 6A, the second 110 and third 112 order harmonics have changed. The deteriorated state of the aged sensor has produced the second order harmonic 110 that is larger than the third order harmonic 112.

One can employ the values found in the graphs of FIGS. 6A and 6B and apply them to the process described in relation to FIG. 5 in order to provide an example of the deterioration effects. For the signal related to the new sensor illustrated in FIG. 6A, the ratio $P_2/P_1=0.0326$, as compared to the ratio $P_2/P_1=0.0425$ for the aged sensor in FIG. 6B. The ratio $P_3/P_2= 1.059$ for the new sensor versus $P_3/P_2=0.4146$ for the aged sensor. And, the ratio of $P_5/P_2=0.0594$ for the new sensor, while $P_5/P_2=0.00937$ for the aged sensor. One will note the significant changes in the ratios of the even/odd harmonics resulting from the aging process. By employing these types of values, then, one can quantitatively determine when a sensor has deteriorated to the point that it is determined to be unacceptable, or that the engine control strategy needs to compensate for the deterioration.

Although two embodiments of the present invention have been described herein, it should be apparent to those skilled in the art that the present invention may be embodied in other specific forms without departing from the spirit or scope of the invention. Particularly, it should be understood that the gas sensor may be, for example, a CO, $NO_x$, $CO_2$ or $SO_2$ sensor which employs a limit cycle control strategy, rather than an oxygen sensor. Also, there are many variations that one may desire to employ regarding the particular harmonics chosen for the ratios and the redundancy of the checks for determining sensor deterioration.

Thus, while certain embodiments of the present invention have been described in detail, those familiar with the art to which this invention relates will recognize various alternative designs and embodiments for practicing the invention as defined by the following claims.

We claim:

1. A method of monitoring deterioration of an oxygen sensor in an exhaust stream of an engine, comprising the steps of:

operating the engine under a condition where an oscillation frequency of air/fuel ratio between rich and lean is determined;

receiving a signal from the sensor;

performing a Fourier Transform on the signal to produce a frequency domain signal having even and odd order harmonics;

calculating, based on the frequency domain signal, respective magnitudes for one of the odd order harmonics and one of the even order harmonics;

calculating, based on the calculated magnitudes, a ratio of the odd order harmonic to the even order harmonic; and comparing the ratio to a corresponding acceptable range of values to monitor changes in a response time and effectiveness of the sensor over time.

2. The method of claim 1, further comprising the step of determining that the sensor has failed when the ratio is outside of the acceptable range.

3. The method of claim 1, wherein the odd order harmonic is a first order harmonic and the even order harmonic is a second order harmonic, and further wherein the ratio of the odd order harmonic to the even order harmonic is a ratio of the first order harmonic to the second order harmonic having a corresponding first acceptable range of values.

4. The method of claim 3, further comprising the steps of:
   calculating a magnitude of a third order harmonic;
   calculating a ratio of the second order harmonic to the third order harmonic; and
   comparing the ratio of the second order harmonic to the third order harmonic to a corresponding second acceptable range of values.

5. The method of claim 4, further comprising the step of determining that the sensor has failed if both ratios are outside their corresponding acceptable range of values.

6. The method of claim 5, further comprising the step of operating the engine if either, but not both, (i) the ratio of the first order harmonic to the second order harmonic is outside the corresponding first acceptable range of values, or (ii) the ratio of the second order harmonic to the third order harmonic is outside the corresponding second acceptable range of values.

7. The method of claim 1, wherein the odd order harmonic is a third order harmonic and the even order harmonic is a second order harmonic, and further wherein the ratio of the odd order harmonic to the even order harmonic is a ratio of the third order harmonic to the second order harmonic having a corresponding first acceptable range of values.

8. The method of claim 7, further comprising the steps of:
   calculating a magnitude of a fifth order harmonic;
   calculating a ratio of the fifth order harmonic to the second order harmonic; and
   comparing the ratio of the fifth order harmonic to the second order harmonic to a second acceptable range of values.

9. The method of claim 8, further comprising the step of determining that the sensor has failed if either (i) the ratio of the third order harmonic to the second order harmonic is outside the corresponding first acceptable range of values, or (ii) the ratio of the fifth order harmonic to the second order harmonic is outside the corresponding second acceptable range of values.

10. The method of claim 9, further comprising the steps of:
    calculating a magnitude of a first order harmonic;
    calculating a ratio of the second order harmonic to the first order harmonic; and
    comparing the ratio of the second order harmonic to the first order harmonic to a third acceptable range of values.

11. The method of claim 10, further comprising the step of determining that the sensor has failed if either (i) the ratio of the third order harmonic to the second order harmonic is outside the corresponding first acceptable range of values, (ii) the ratio of the fifth order harmonic to the second order harmonic is outside the corresponding second acceptable range of values, or (iii) the ratio of the second order harmonic to the first order harmonic is outside the corresponding third acceptable range of values.

12. The method of claim 1, wherein the odd order harmonic is a fifth order harmonic and the even harmonic is a second order harmonic.

13. The method of claim 1, wherein the step of operating the engine comprises the step of forcing the air/fuel ratio to oscillate between rich and lean at a predetermined frequency.

14. The method of claim 1, wherein the step of operating the engine comprises the steps of:
    operating the engine in a steady-state mode; and
    determining a frequency of oscillation of the air/fuel ratio between rich and lean.

15. A method of monitoring deterioration of an oxygen sensor in an exhaust stream of an engine, comprising the steps of:
    operating the engine under a condition where an oscillation frequency of air/fuel ratio between rich and lean is determined;
    receiving an oxygen signal from an oxygen sensor;

performing a Fourier Transform on the oxygen signal to produce a frequency domain signal having even and odd order harmonics;

calculating respective magnitudes of two of the odd order harmonics and one of the even order harmonics;

calculating a first ratio of a first one of the odd harmonics to the even order harmonic;

comparing the first ratio to a first acceptable range of values;

calculating a second ratio of a second one of the odd order harmonics to the even order harmonic; and comparing the second ratio to a second acceptable range of values to monitor changes in a response time and effectiveness of the sensor over time.

16. The method of claim 15, further comprising the step of determining that the sensor has failed if either (i) the first ratio is outside the first acceptable range of values, or (ii) the second ratio is outside the second acceptable range of values.

17. The method of claim 15, further comprising the step of determining that the sensor has failed if both of the first and second ratios are outside their corresponding acceptable range of values.

18. The method of claim 15, wherein the step of operating the engine comprises the step of forcing the air/fuel ratio to oscillate between rich and lean at a predetermined frequency.

19. An apparatus for determining deterioration of an oxygen sensor in an exhaust stream from an engine in a vehicle, the apparatus comprising:

an oxygen sensor mounted within the exhaust stream for producing an oxygen signal;

means for receiving the oxygen signal;

means for performing a Fourier Transform on the oxygen signal to produce a frequency domain signal having even and odd order harmonics;

means for calculating respective magnitudes of one of the odd order harmonics and one of the even order harmonics;

means for calculating a ratio of the odd order harmonic to the even order harmonic; and means for comparing the ratio to an acceptable range of values to monitor changes in a response time and effectiveness of the sensor over time.

20. The apparatus of claim 19, wherein the oxygen sensor is a zirconia based oxygen sensor.

* * * * *